United States Patent [19]

Pallos et al.

[11] Patent Number: 4,532,348
[45] Date of Patent: Jul. 30, 1985

[54] 1-(SUBSTITUTED PHENYLTHIOCARBAMYL) 3,3-DISUBSTITUTED FORMAMIDINES AND THEIR USE AS PHARMACEUTICAL AGENTS

[75] Inventors: Ferenc M. Pallos, Walnut Creek; Jack R. DeBaun, Sunnyvale; Eugene G. Teach, El Cerrito, all of Calif.

[73] Assignee: Stauffer Chemical Company, Westport, Conn.

[21] Appl. No.: 169,350

[22] Filed: Jul. 16, 1980

Related U.S. Application Data

[63] Continuation of Ser. No. 42,180, May 29, 1979, abandoned, which is a continuation-in-part of Ser. No. 22,130, Mar. 20, 1979, abandoned.

[51] Int. Cl.³ .......................................... C07C 157/09
[52] U.S. Cl. ..................... 564/27; 546/190; 546/231; 544/58.1; 544/58.6; 544/111; 544/160; 544/359; 544/400; 548/523; 548/567; 260/239 BF
[58] Field of Search ........................................ 564/27

[56] References Cited

U.S. PATENT DOCUMENTS 3,898,277  8/1975  Duerr et al. ................... 260/552 R
3,933,833  1/1976  Trepanier et al. .......... 260/552 R X
3,959,368  5/1976  DeBaun et al. ............... 260/552 SC
4,012,527  3/1977  DeBaun et al. .......... 260/552 SC X Primary Examiner—Charles F. Warren
Attorney, Agent, or Firm—Edwin H. Baker

[57] ABSTRACT 1-(Substituted phenylthiocarbamyl) 3,3-disubstituted formamidine compounds having the structural formula

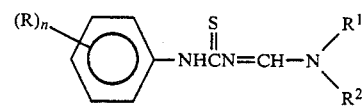

wherein
n is 1, 2 or 3,
R is alkyl having 1 to 6 carbon atoms, alkoxy having 1 to 6 carbon atoms, alkylthio having 1 to 4 carbon atoms, halogen, nitro, acyl having 1 to 4 carbon atoms, hydroxyl and

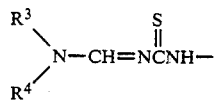

wherein $R^3$ and $R^4$ have the same meaning as $R^1$ and $R^2$ defined below,
$R^1$ and $R^2$ are the same or different and are alkyl having 1 to 6 carbon atoms, or taken together represent the chain $-(CH_2)_p-(X)_m-(CH_2)_q$ and forming a ring structure with the nitrogen to which they are bound wherein p is 1, 2 or 3, q is 2 or 3, X represents $-O-$, $-S-$, $-SO-$, $-SO_2-$, $-NR^3-$, $R^3$ is hydrogen or alkyl having 1 to 6 carbon atoms, and m is 0 or 1 and their use as pharmaceutical agents.

2 Claims, No Drawings

1-(SUBSTITUTED PHENYLTHIOCARBAMYL) 3,3-DISUBSTITUTED FORMAMIDINES AND THEIR USE AS PHARMACEUTICAL AGENTS

CROSS-REFERENCE TO RELATED APPLICATION

This is a continuation of application Ser. No. 042,180, filed May 29, 1979, now abandoned, which is a continuation-in-part of application Ser. No. 022,130, filed Mar. 20, 1979, now abandoned.

BACKGROUND OF THE INVENTION

1. Prior Art

U.S. Pat. No. 3,959,368 teaches the compound N,N-dimethyl-N'-phenylthiocarbamyl formamidine and its use as an antiinflammatory.

2. Brief Description of the Invention

The compounds of this invention have the following structural formula:

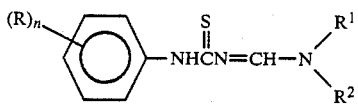

wherein n is the integer 1,2 or 3, preferably 1 or 2;

R is alkyl having 1 to 6 carbon atoms, preferably 1 to 4 carbon atoms, more preferably methyl; alkoxy having 1 to 6 carbon atoms, preferably 1 to 4 carbon atoms, more preferably methoxy; alkylthio having 1 to 4 carbon atoms, preferably methylthio; halogen, preferably chlorine; nitro; acyl having 1 to 4 carbon atoms, preferably acetyl; hydroxyl and

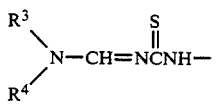

wherein $R^3$ and $R^4$ have the same meaning as $R^1$ and $R^2$ defined below;

$R^1$ and $R^2$ are the same or different and are alkyl having 1 to 6 carbon atoms, preferably 1 to 3 carbon atoms, more preferably methyl or taken together represent the chain $-(CH_2)_p-(X)_m-(CH_2)_q$ and forming a ring structure with the nitrogen to which they are bound wherein p is 1, 2 or 3, q is 2 or 3, X represents $-O-$, $-S-$, $-SO-$, $-SO_2-$, $-NR^3-$, $R^3$ is hydrogen or alkyl having 1 to 6 carbon atoms, preferably methyl, and m is 0 or 1.

The compounds of this invention can be used for their intended pharmaceutical purposes either as the free base (described above) or in the form of suitable organic or inorganic acid salts. A preferred form is the hydrochloric acid salt.

The compounds of this invention can be prepared according to the following reaction:

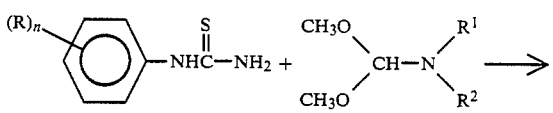

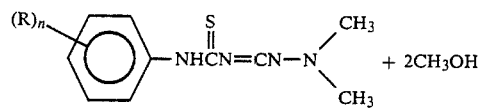

wherein R, $R^1$, $R^2$ and n are as defined.

Generally, the reaction is carried out by dissolving the two reactants in a solvent such as benzene or toluene, heating the solution at reflux for about 15 minutes, slowly distilling off the solvent-methanol mixture, cooling the undistilled solution to room temperature and the recovering of the desired product by filtration. The recovered product can be purified by standard procedures.

Preparation of the compounds of this invention is illustrated by the following example.

EXAMPLE 1

1-(p-methoxyphenylthiocarbamyl) 3,3-dimethyl formamidine hydrochloride

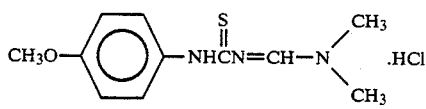

7.3 grams (g) p-methoxyphenylthiourea and 5.0 g dimethylformamide dimethyl acetal and 100 milliliters (ml) benzene were placed in a reaction flask equipped with a distillation head. The mixture was gently refluxed for 15 minutes with the slow removal of the benzene methanol azeotrope mixture through the distillation head. After cooling, the formed 8.0 g precipitate was recovered by filtration with a melting point (m.p.) 140°–142° C. The filtrate was treated with a cold ether/HCl mixture and 1.0 g precipitated hydrochloride filtrate was recovered with a m.p. 150° C. with decomposition (dec.).

The following is a table of certain selected compounds that were prepared according to the procedure described herein. Compound numbers are assigned to each compound and are used throughout the remainder of the specification.

TABLE 1

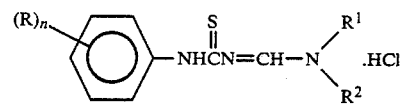

| Compound Number | n | R | $R^1$ | $R^2$ | m.p. °C. |
|---|---|---|---|---|---|
| 1 | 1 | 4-CH$_3$O | CH$_3$ | CH$_3$ | 150 dec. |
| 2 | 1 | 4-Cl | CH$_3$ | CH$_3$ | 170 dec. |
| 3 | 2 | 2,6-C$_2$H$_5$ | CH$_3$ | CH$_3$ | 167-8 dec. |
| 4 | 2 | 2,4-CH$_3$ | CH$_3$ | Ch$_3$ | 170-1 dec. |
| 5 | 1 | 4-NO$_2$ | CH$_3$ | CH$_3$ | 169–174° |
| 6 | 1 | 4-CH$_3$C(=O) | CH$_3$ | CH$_3$ | 174–176° |
| 7 | 1 | 4-HO | CH$_3$ | CH$_3$ | |
| 8 | 2 | 3,4-CH$_3$ | CH$_3$ | CH$_3$ | 179–181° |
| 9 | 2 | 3,4-Cl$_2$ | CH$_3$ | CH$_3$ | 176–179° |
| 10 | 1 | 3-Cl | CH$_3$ | CH$_3$ | 173–177° |
| 11 | 1 | 2-Cl | CH$_3$ | CH$_3$ | 180–183° |
| 12 | 2 | 2,5-CH$_3$O | CH$_3$ | CH$_3$ | 175–178° |
| 13 | 1 | 4-C$_2$H$_5$ | CH$_3$ | CH$_3$ | 182–184° |
| 14 | 2 | 2,6-CH$_3$ | CH$_3$ | CH$_3$ | 172–175° |

TABLE 1-continued $$(R)_n\text{-}C_6H_4\text{-}NHCN=CH-N(R^1)(R^2) \cdot HCl$$
(with S double-bonded to the C of NHCN)

| Compound Number | n | R | R¹ | R² | m.p. °C. |
|---|---|---|---|---|---|
| 15 | 2 | 2,6-Cl₂ | CH₃ | CH₃ | 177–180° |
| 16 | 2 | 2,4-Cl₂ | CH₃ | CH₃ | 180–182° |
| 17 | 1 | 2-CH₃O | CH₃ | CH₃ | 173–175° |
| 18 | 1 | 3-CH₃O | CH₃ | CH₃ | 163–166° |
| 19 | 2 | 2,4-CH₃ | —CH₂CH₂CH₂CH₂CH₂— | | 145–151° |
| 20 | 1 | * | CH₃ | CH₃ | 190–193° |

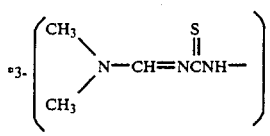

Anti-Inflammatory Screening

Anti-inflammatory activity for a compound is demonstrated by either one of two tests. The first test is for adjuvant arthritis inhibition and the second, an antiedema test, involves the diminution of experimental edema induced in the hind paw of a rat by the injection of carrageenin.

Adjuvant Arthritis Inhibition

This test was run according to the test procedure recited by VanArman, G. C., Nuss, G. W. and Risley, E. A., J. Pharmacol. Exper. Terap., 187:400–413, 1973. The following is a description of the test:

The hind-foot volumes of five Wistar male rats (Taiwan strain) weighing 130–160 g each were measured by fluid displacement immediately prior to intraplantar administration (right hind paw) of 0.1 ml of an adjuvant suspension containing 5 milligrams (mg) *Mycobacterium butyricum bacilli* suspended in heavy mineral oil. Test compounds were orally administered to the animals for five days beginning the day before injection of the adjuvant. Four hours after the fifth daily drug dose the volume of the right hind paw (primary lesion) was measured for determination of any acute anti-inflammatory effect. Fourteen days after adjuvant inoculation the volume of the uninjected foot was measured (secondary lesion) for determination of prolonged anti-inflammatory effect or immunosuppressant effect. The percent reduction in foot volume was calculated for each hind paw in relation to corresponding control values determined simultaneously. A greater than 30 percent reduction in volume of either paw is considered a significant effect. Reduction of the primary lesion without effect on the secondary lesion denotes acute anti-inflammatory activity of short to moderate duration. Reduction of the secondary lesion without effect on the primary lesion suggests interference with the immunological component of polyarthritis disease. Reduction of both lesions suggests anti-inflammatory activity of long duration or a mixture of anti-inflammatory and immunosuppressant effects as occurs with corticosteroids.

Table 2 shows the reduction in edema of the primary and secondary lesions according to the above-described test procedure at the indicated rate.

TABLE 2

| Compound Number | Rate mg/kg | Primary | Secondary |
|---|---|---|---|
| 1 | 5 | 39% | 35% |
| 2 | * | | |
| 3 | 100 | 39% | 31% |
| 4 | 100 | 0% | 0% |

*Not tested

Anti-edema

Anti-edema effect was determined according to the test procedure recited by Winter, C. A., Risley, E. A., and Nuss, G. W., Proc. Exper. Biol. Med. 111:544–547, 1962. For this test, three male Wistar rats (Taiwan strain) weighing 100–120 g each are orally dosed with test compound dissolved or suspended in 3 ml of water. One hour later, the plantar surface of the right hind paw was injected with 0.1 ml of a 1 percent suspension of carrigeenan in saline and the left paw was similarly injected with saline only. Three hours after the injection the volume of both hind paw was measured by fluid displacement and the percent decrease in carrigeenan-induced swelling (volume of carrigeenan injected foot minus saline injected foot) was determined by comparison with untreated (no test compound) animals. Greater than 30 percent inhibition is considered evidence of an anti-edema effect.

Table 3 shows the reduction in edema in the hind paw of a rat according to the above-described test procedure at the rate indicated.

TABLE 3

| Compound Number | Rate mg/kg | Reduction of Induced Edema |
|---|---|---|
| 1 | 5 | 35% |
| 2 | 25 | 32% |
| 3 | 100 | 33% |
| 4 | * | |
| phenylbutazone (standard) | 100 | 41% |

*Not tested

Anti-Hypertensive Screening

This test was run according to the test procedure recited by Nagoaka, A., Kikuchi, K. and Aramaki, Y., Jap. J. Pharmacol., 19:401–408, 1969. For this test, two normotensive Wistar rats (Taiwan strain) were placed in perspex holders and then placed in a heated chamber at 40° C. for 4–6 minutes before treatment. They were maintained there throughout each experiment. Systolic blood pressure was recorded by indirect means employing a tail cuff and pneumatic sensor device applied to the base of the animal's tails. The device was coupled to a programmed Narco-Biosystems sphygmomano meter (Model PE-300), an instrument for measuring blood pressure, and Sanei polygraph. After recording suitably steady blood pressure readings, test drugs were orally administered and blood pressure checked again 2, 4 and 6 hours after drug administration. A mean decrease of more than 10 percent from the pretreatment value at any two consecutive measurement intervals is considered evidence of hypotensive effect.

The results of the anti-hypertensive test are reported in Table 4.

TABLE 4

| Compound Number | Rate mg/kg | Percent Mean Decrease in Systolic Blood Pressure | | |
|---|---|---|---|---|
| | | 2 hours | 4 hours | 6 hours |
| 1–3 | * | | | |
| 4 | 100 | 4% | 17% | 15% |
| α-methyl 3,4-dihydroxy-phenylalanine (standard) | 100 | 11% | 21% | 19% |

*decreases of less than 10% were observed for compounds 1–3 and are not reported The compounds of the present invention, either alone or in the form of pharmaceutical composition may be administered to an animal subject in any of a number of forms and via any of several routes. Thus, the compounds or compositions thereof may be orally administered in the form of tablets, pills, capsules, or in the form of a suspension. The compounds may also be administered parenterally in the form of an injectable solution or suspension. The compounds or compositions thereof may also be administered topically, in the form of an ointment or rectally, in the form of a suppository.

When orally administering the compounds or compositions, use can be made of a tablet, pill or capsule consisting entirely of the desired compound, although ordinarily, a composition comprising an effective amount of the compound and varying amounts of one or more physiologically inert materials such as carriers, vehicles, binders and the like will be used. Additionally, the compounds may be orally administered in the form of a suspension thereof in a suitable vehicle such as a syrup.

When parenterally administering the compounds or compositions, use may be made of a parenteral solution or suspension of the compound in a suitable solvent or suspension medium.

The compounds of the present invention may also be administered rectally in the form of a suppository comprising an effective amount of the desired compound and a suitable vehicle such as petroleum jelly.

What we claim:

1. The commpound having the structural formula

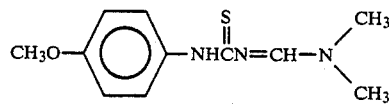

or salts thereof formed by combination with a suitable organic or inorganic acid.

2. The compound having the structural formula

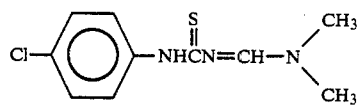

or salts thereof formed by combination with a suitable organic or inorganic acid.

* * * * *